United States Patent [19]

Schendel et al.

[11] 4,374,657

[45] Feb. 22, 1983

[54] PROCESS OF SEPARATING ACID GASES FROM HYDROCARBONS

[75] Inventors: Ronald L. Schendel, Hermosa Beach; Frederic T. Selleck, Whittier, both of Calif.

[73] Assignee: Fluor Corporation, Irvine, Calif.

[21] Appl. No.: 270,016

[22] Filed: Jun. 3, 1981

[51] Int. Cl.³ .............................................. B01D 59/12
[52] U.S. Cl. ............................................ 62/19; 55/16; 55/158; 62/28; 62/30
[58] Field of Search ............ 62/14, 15, 19, 25, 27–30, 62/32; 55/16, 68, 73, 158, 66

[56] References Cited

U.S. PATENT DOCUMENTS 3,320,753 5/1967 Bray et al. ............................... 62/28
4,264,338 4/1981 Null ........................................ 55/16

Primary Examiner—Frank Sever
Attorney, Agent, or Firm—Lyon & Lyon

[57] ABSTRACT

A process of separating acid gases consisting of carbon dioxide and/or hydrogen sulfide from hydrocarbons is disclosed. Methane is first separated from the hydrocarbon stream to produce a substantially methane free hydrocarbon stream containing acid gases, ethane and heavier hydrocarbon components. The substantially methane free hydrocarbon stream is thereafter passed through a semipermeable membrane system to separate the acid gases from the ethane and heavier hydrocarbon components.

16 Claims, 4 Drawing Figures

PROCESS OF SEPARATING ACID GASES FROM HYDROCARBONS

BACKGROUND OF THE INVENTION

Many hydrocarbon gas streams, in addition to the predominant methane component, contain varying amounts of heavier hydrocarbons such as ethane, propane, butane, etc., as well as impurities such as acid gases which are typically carbon dioxide and/or hydrogen sulfide. It is often necessary to process such hydrocarbon streams to remove the impurities and to separate the heavier hydrocarbon components which are also valuable and quite often have different end uses than methane. Thus, for example, in order for natural gas to be commercially acceptable, it must meet stringent specifications with respect to heating value and hydrogen sulfide and carbon dioxide contents. Consequently, sufficient hydrogen sulfide must be removed so that the natural gas has a hydrogen sulfide concentration of no more than about one quarter to about one half grain per 100 standard cubic feet. By the same token, the carbon dioxide content should be less than about 2 mole percent, since higher concentrations can be corrosive and may reduce the heating value of the natural gas to an unacceptable level.

Removal of acid gases from hydrocarbons may be undertaken by use of a number of established technologies. Thus, for example, it is known to use physical solvents which are selective toward the acid gas components and chemical solvents which will react with such components. Examples of appropriate physical solvents include propylene carbonate and the dimethyl ether of polyethyleneglycol. Examples of suitable chemical solvents are aqueous solutions of potassium carbonate and of amines such as monoethanolamine, diethanolamine, etc. More recently, it has been proposed to use semipermeable membranes, as in U.S. Pat. No. 4,130,403. However, it is not considered economical to produce large membrane elements or units, and consequently, membrane systems do not enjoy the same economy of scale that conventional processing enjoys and their use for large scale applications has been limited.

There are also several methods which are known to remove hydrocarbon components heavier than methane. In some instances, merely cooling the hydrocarbon stream will condense part of the heavier components to liquids which may then be separated from the uncondensed portion and further separated into the individual components, e.g., ethane, propane, butane, etc. Another method for recovery of such hydrocarbon liquids is by absorption in a hydrocarbon oil. In this method, ethane and the other heavier components are dissolved in oil in an absorber. The oil containing the dissolved components then flows to a stripper in which the hydrocarbon components are desorbed by the application of heat.

The most recently developed technology for separating and recovering the hydrocarbon liquids is carried out at cryogenic temperatures in which the refrigeration may be supplied, at least in part, by expanding the gas while performing work in a device called a turboexpander. The condensed liquids may then be separated by low temperature distillation.

If the hydrocarbon stream also contains carbon dioxide and/or hydrogen sulfide, such components are usually removed prior to separation of the hydrocarbon liquids. In the case of separation at cryogenic temperatures, the acceptable and preferred practice is to remove the carbon dioxide and any water vapor that may be present prior to cooling, since both water and carbon dioxide can become solid at low temperature and thereby plug the equipment. Under certain conditions, however, carbon dioxide will remain in the liquid state, and its separation by distillation may be preferrable to other methods. Thus, in U.S. Pat. No. 3,595,782, a process is described in which water is removed before the gas stream encounters cryogenic temperatures, but the carbon dioxide is separated from the condensed liquid by distillation at low temperature. In such process, the carbon dioxide is removed overhead along with methane, while ethane and heavier hydrocarbon components are removed as a bottom product of the distillation. This process has a disadvantage, however, in that the carbon dioxide remains with the methane and must ultimately be separated therefrom, unless the carbon dioxide content is relatively low. Also, if hydrogen sulfide is not removed before the gas is cooled, it will be separated as a liquid along with the heavier hydrocarbon liquids, and if the individual hydrocarbon components are subsequently separated, the hydrogen sulfide will appear with the hydrocarbons, primarily the propane and ethane, and must then be removed therefrom.

SUMMARY OF THE INVENTION

The present invention is a process of separating acid gas components from a hydrocarbon stream in which methane is first separated to produce a substantially methane free hydrocarbon stream. Preferably, such separation is achieved by low temperature distillation in which the methane is removed as overhead, while ethane, heavier hydrocarbon components, and the acid gases are removed as a liquid bottoms product. The substantially methane free hydrocarbon stream is then passed through a semipermeable membrane system to separate the acid gases from the hydrocarbon components.

Because methane is present in significant quantities prior to its separation, the acid gas concentration in the hydrocarbon stream is increased significantly when methane is separated by the distillation process. The substantially methane free hydrocarbon stream containing the acid gases may be further distilled to separate the hydrocarbon components and/or concentrate further the acid gas components, as will be described in more detail and illustrated by the working examples which follow.

Although the carbon dioxide and hydrogen sulfide contents may be separated by using the different technologies described above, because the concentration of such components is increased and the total volume of hydrocarbon gas stream reduced, the equipment required for such separation is likewise greatly reduced. Moreover, the intentional removal of methane in the process of this invention provides a hydrocarbon stream which is especially well suited to processing with semipermeable membranes for removal of acid gas components. By the same token, the combination of first removing methane and subsequently processing the remaining hydrocarbon stream with a membrane system provides a significant economic advantage. Thus, while hydrocarbons heavier than methane are more soluble than methane in solvents used to remove acid gas components and represent a significant loss, most membranes reject the heavier hydrocarbon components even easier than methane. For example, the separation of carbon dioxide from methane with cellulose acetate membranes relies on the fact that carbon dioxide will permeate the membrane approximately 25 times faster than methane under equal driving force. With methane removed, the carbon dioxide is separated from a stream containing only ethane and heavier hydrocarbon components and will permeate the same membrane approximately 75 times faster than ethane. Stated otherwise, the ethane will pass through the cellulose acetate membrane three times slower than methane, and propane and heavier hydrocarbon components will slip through at an even slower rate.

In a preferred embodiment, the bottom liquid product from the distillation step in which methane is separated is further distilled to produce an overhead product which contains all of the acid gas components and, in the case where carbon dioxide is the only such component, may be the approximate binary azeotrope of carbon dioxide and ethane depending upon the economics of the system and the process variables. Previously, such an azeotrope was regarded as a complicating factor, but in the process of the present invention, the azeotrope may be handled in a manner which contributes to the overall effectiveness and economy of the technology. Thus, a recycled stream of ethane and/or heavier hydrocarbons is obtained which may be returned to the low temperature distillation column to ensure the operation of that column without the danger of the formation of solid carbon dioxide.

The second distillation concentrates the acid gas components further which is advantageous insofar as the removal of such components is concerned. Additionally, the overhead product of the distillation is very clean, which in turn is extremely advantageous in that particulates and heavy viscous contaminants decrease membrane life drastically. The distillation step, therefore, acts as an efficient pretreatment which greatly enhances the life of the membranes, which is significant because membrane replacement can be the single greatest operating expense in a membrane plant.

The process of this invention, additionally, is of particular significance where the recovery of hydrocarbon components heavier than methane, i.e., ethane, propane, butane, etc. (the natural gas liquids), as separate products is desired. The process is also useful to remove carbon dioxide and/or hydrogen sulfide with part of all of the heavier hydrocarbon components blended back into the methane stream.

DESCRIPTION OF THE PREFERRED EMBODIMENTS

Figure 1:
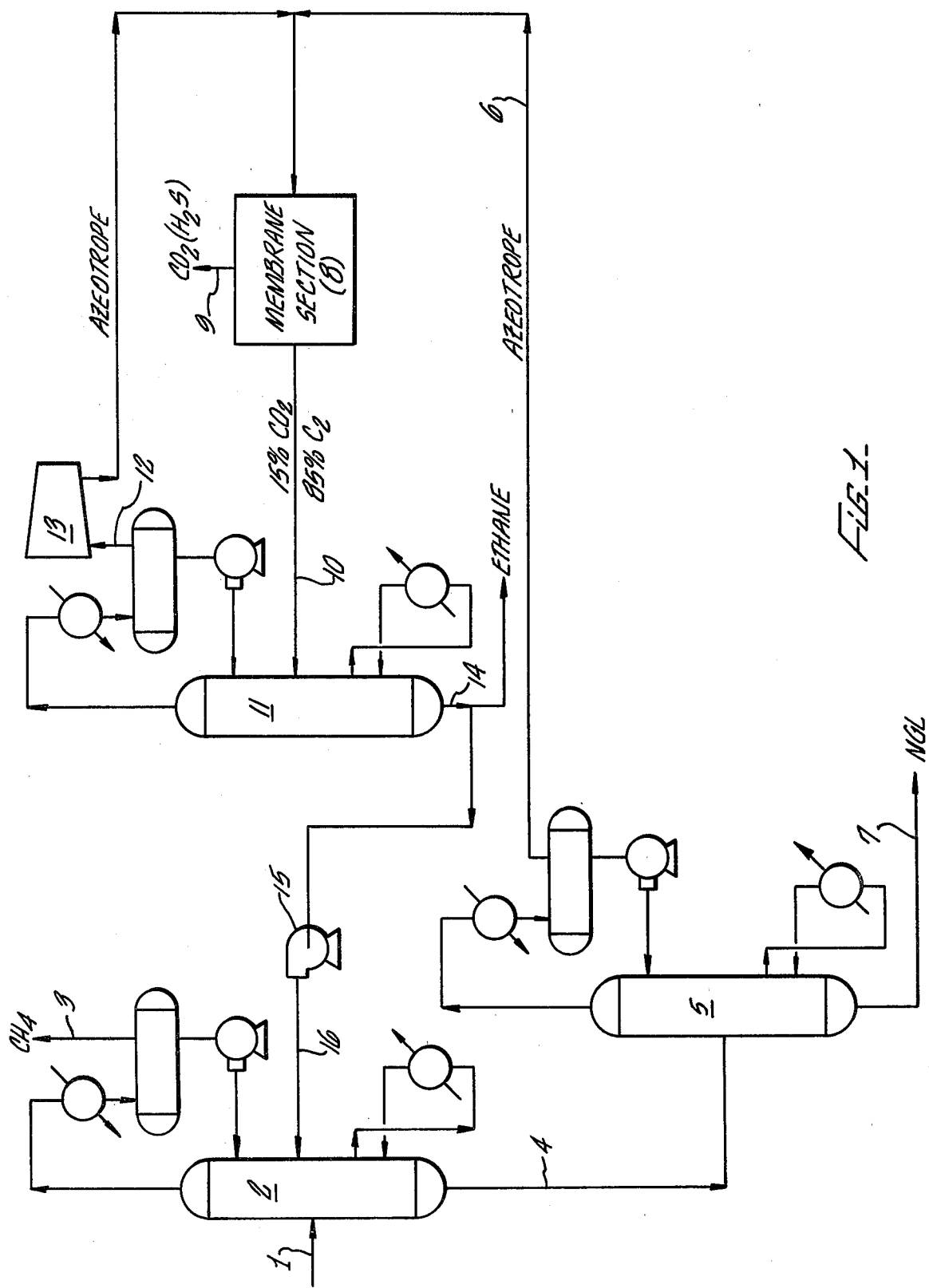
FIGS. 1 through 4 are schematic illustrations of embodiments of the process of this invention.

In accord with the process of this invention, acid gases consisting essentially of carbon dioxide and/or hydrogen sulfide may be removed from a hydrocarbon stream comprising methane, ethane and heavier hydrocarbon components or a mixture of such hydrocarbons as, for example, natural gas. The hydrocarbon stream may be a naturally occurring stream such as natural gas or gases produced with crude oil, i.e., associated gases, or synthetic gases produced from refinery operations. The methane content is removed from the hydrocarbon stream, preferably by a low temperature distillation, that is a temperature less than approximately $-85°$ F., and a pressure within the range of approximately 300 to about 700 psia. The methane is removed from the distillation column as the principal overhead product, and a substantially methane free stream comprising ethane and heavier hydrocarbon components and the acid gases is recovered as the bottom product. The substantially methane free bottom product is fed through one or more semipermeable membrane systems to separate the acid gas components and produce a hydrocarbon rich stream of ethane, propane, butane, etc. The exact composition of the hydrocarbon rich stream, of course, will depend upon the composition of the initial hydrocarbon feed stream, i.e., its respective ethane and heavier components content.

The semipermeable membrane used in this invention may be cellulose acetate, cellulose diacetate, cellulose triacetate, cellulose propionate, cellulose butyrate, cellulose cyanoethylate, cellulose methacrylate, or mixtures thereof, as described in U.S. Pat. No. 4,130,403. Other semipermeable membrans which provide a separation between acid gases and ethane or heavier hydrocarbons that is more effective than the separation between acid gases and methane may also be used.

Preferably the membrane used is a thin dried support cellulose ester membrane having a permeability constant of at least $10^{-8}$ (measured at 100 psi) for $H_2$ or $CO_2$. In this separation, the differential pressure across the membrane should be at least 100 psi and the partial pressure of $CO_2$ and $H_2S$ should be maintained at a higher level on the feed side of the membrane than on the permeate side. Preferably, the partial pressure of $CO_2$ and $H_2S$ in the permeate stream should be at most about 80% of the partial pressure of those same components in the feed stream.

In gas separation processes employing semipermeable membranes, the gaseous mixture is brought into contact with one side of a membrane and a sufficient positive pressure differential is maintained across the membrane such that the more permeable gaseous components of the mixture are driven from the feed side of the membrane to the permeate side. These more permeable components pass through the membrane at a higher rate than do other components of the feed mixture which have lower permeabilities. Also, the partial pressure of the more permeable components is maintained at a higher level on the feed side of the membrane than on the permeate side by separately removing the residue of the feed stream and the permeate stream from contact with the membrane.

Following the semipermeable membrane step, the hydrocarbon rich stream is further processed, as for example, by an additional distillation procedure, to produce a stream of ethane and/or heavier hydrocarbon components which may be recycled to the first distillation to prevent the carbon dioxide in the hydrocarbon stream therein from freezing and plugging the distillation column.

The process of the present invention will be further understood by reference to the following specific but illustrative examples in which reference is made to the Figures of drawing to illustrate different embodiments of such process.

EXAMPLE I

Referring to FIG. 1, a hydrocarbon stream of the following composition enters the process as stream 1, which is fed to a distillation column 2 at a pressure of approximately 565 psia:

| | |
|---|---|
| N$_2$ | 0.5 Vol. % |
| CH$_4$ | 74.0 Vol. % |
| CO$_2$ | 12.7 Vol. % |
| C$_2$ | 6.5 Vol. % |
| C$_3$ | 3.5 Vol. % |
| C$_4$ and higher | 2.8 Vol. % |

The coldest temperature within column 2 is approximately −115° F. Methane is taken as the principal overhead product, stream 3, and has the following composition:

| | |
|---|---|
| N$_2$ | .6 Vol. % |
| CH$_4$ | 95.2 Vol. % |
| CO$_2$ | 1.8 Vol. % |
| C$_2$ | 2.4 Vol. % |

The bottoms product 4 is fed to a second distillation column 5 at a pressure only slightly less than the first distillation column as a result of frictional losses in the piping, about 535 psia. The overhead of this distillation 6 is approximately the binary azeotrope formed by carbon dioxide and ethane:

| | |
|---|---|
| C$_1$ | Trace |
| CO$_2$ | 66.0 Vol. % |
| C$_2$ | 34.0 Vol. % |
| C$_3$ | Trace |

The bottoms product of this distillation 7 is the remaining ethane plus higher hydrocarbons (natural gas liquids) which may be further distilled into separate components or blended back with the methane 3.

The overhead product 6 is fed to a membrane plant 8 at a pressure only slightly less than the second distillation column, again as a result of frictional losses in the piping, about 485 psia.

In the membrane plant 8, the gases pass over a semipermeable membrane through which the carbon dioxide passes much more readily than ethane. The surface area of membrane available and residence time are controlled so that a stream 9 containing 98% CO$_2$ at low pressure, e.g. 5 to 10 psig, is produced. Using a cellulose acetate membrane as an example, the hydrocarbon stream which does not pass through the membrane 10 exits with 91% of the CO$_2$ removed and an approximate composition of:

| | |
|---|---|
| 15 Vol. % | CO$_2$ |
| 85 Vol. % | C$_2$ |

The pressure is only slightly less than the entering gas due to frictional losses, in this case, about 480 psia.

The gas exiting the membrane system 10 rich in ethane is fed to a third distillation column 11 at a pressure only slightly less than that of the exit pressure of the membrane system due to frictional losses in the line, about 475 psia. The overhead product from this distillation 12 is again approximately the binary azeotrope of ethane and carbon dioxide which is compressed 13 to overcome the 10–20 psi of frictional loss encountered and returned to the entrance of the membrane system 8. The bottoms product 14 is ethane, a portion of which is pumped 15 back to the distillation column 2 as the hydrocarbon recycle 16 which prevents the CO$_2$ from freezing in the distillation column.

EXAMPLE II

Figure 2:
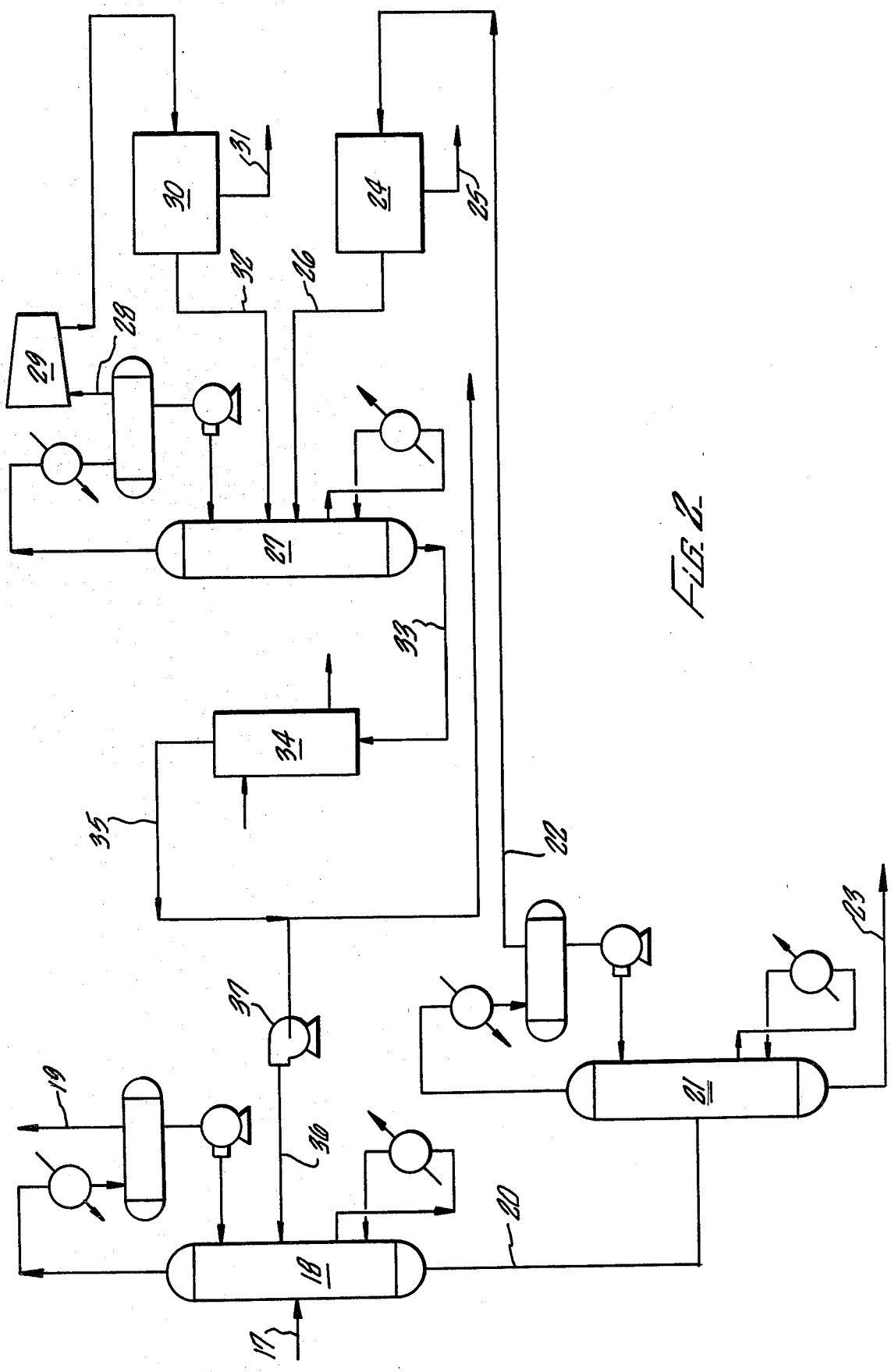

As shown in FIG. 2, a hydrocarbon stream containing H$_2$S and CO$_2$, of the following composition, enters the process as stream 17, which is fed to a distillation column 18:

| | |
|---|---|
| N$_2$ | .5 Vol. % |
| CH$_4$ | 71.2 Vol. % |
| CO$_2$ | 12.2 Vol. % |
| C$_2$ | 6.3 Vol. % |
| H$_2$S | 4.0 Vol. % |
| C$_3$ | 3.4 Vol. % |
| C$_4$ and higher | 2.4 Vol. % |

In this case, the pressure is about 565 psia and the coldest temperature within column 18 is approximately −115° F. Methane is taken as the principal overhead product, stream 19, and has the following composition:

| | |
|---|---|
| N$_2$ | .6 Vol. % |
| CH$_4$ | 95.2 Vol. % |
| CO$_2$ | 1.8 Vol. % |
| H$_2$S | Trace |
| C$_2$ | 2.4 Vol. % |

The bottom product 20 is fed to a second distillation column 21 at a pressure only slightly less than the first distillation column as a result of frictional losses in the piping, about 535 psia. The overhead product of the distillation 22 contains all the acid gas (H$_2$S and CO$_2$), ethane, and either some or all of the propane depending on the hydrocarbon products desired. In this example, the concentration of acid gas is maximized and the propane is divided with enough propane going overhead 22 to cause all the H$_2$S to go overhead and the remaining propane to go out the bottom 23 with the butanes and heavier hydrocarbons. The overhead product 22 has the following composition:

| | |
|---|---|
| C$_2$ | 23 Vol. % |
| CO$_2$ | 54 Vol. % |
| C$_3$ | 3 Vol. % |
| H$_2$S | 20 Vol. % |

The overhead product 22 is now fed to a membrane plant 24 at a pressure only slightly less than the second distillation column as a result of a frictional losses in the piping, approximately 485 psia.

In the membrane plant 24, the gases pass over a semipermeable membrane through which the hydrogen sulfide and carbon dioxide pass much more readily than ethane or propane. The surface area of membrane available and residence time are controlled so that a stream 25 containing 98% acid gas (CO$_2$ and H$_2$S) and 2% hydrocarbon (ethane plus propane) at low pressure 5 to 10 psig is produced.

Because H$_2$S will pass through the membrane more readily than even CO$_2$, there is a concentrating effect, and the ratio of CO$_2$ to H$_2$S is less than the ratio of CO$_2$ to H$_2$S in the feed 22. This is beneficial if this gas is to be processed in a Claus plant to produce sulfur.

The hydrocarbon stream 26 which exits the membrane plant without passing through the membranes is now at a pressure only slightly less than the entering gas due to frictional losses, about 480 psia. This stream 26 is fed to a third distillation column 27 in which the binary azeotrope of carbon dioxide with the approximate composition of

| $CO_2$ | 66.0 Vol. % |
|---|---|
| $C_2$ | 34.0 Vol. % | is taken overhead as stream 28, compressed at 29 to overcome frictional losses, and sent to the entrance of a second membrane plant 30.

Carbon dioxide passes through the membrane much more readily than the ethane. Membrane area and residence time are controlled to produce a stream 31 containing 98% $CO_2$ and 2% ethane at a pressure suitable for further processing or venting, in this case, 5 psig. The gas which does not pass through the membrane 32 is now rich in ethane, with the following composition

| 85 Vol. % | $C_2$ |
|---|---|
| 15 Vol. % | $CO_2$ | and exits at a pressure only slightly less than the gas entering the membrane plant. This stream 32 returns to the third distillation column 27.

The bottoms product 33 of the third distillation column, which contains small amounts of hydrogen sulfide not removed by the membrane plant 24, is fed to a contactor 34 where the remaining $H_2S$ is removed by conventional means using caustic, amines or other suitable solvent or reactant. The exit stream 35 contains ethane plus propane and is now free of hydrogen sulfide. A portion of this stream 36 is pumped 37 up to the first distillation column 18 as the hydrocarbon stream required to prevent $CO_2$ freezing.

EXAMPLE III

In some cases, hydrogen sulfide may be present, but in such small quantities relative to $CO_2$ that the process scheme of Example II produces an acid gas stream not suitable as a feed for conventional sulfur producing technology (Claus plant), even with the concentrating effect of $H_2S$ over $CO_2$ in the membrane plant. In such case, sulfur may be produced by special handling of the acid gas stream dilute in $H_2S$, or the $CO_2$ and $H_2S$ may be separated by distillation as shown in this Example and the $H_2S$ removed from the hydrocarbon stream by either membranes or conventional processing such as caustic or amine treating.

Figure 3:
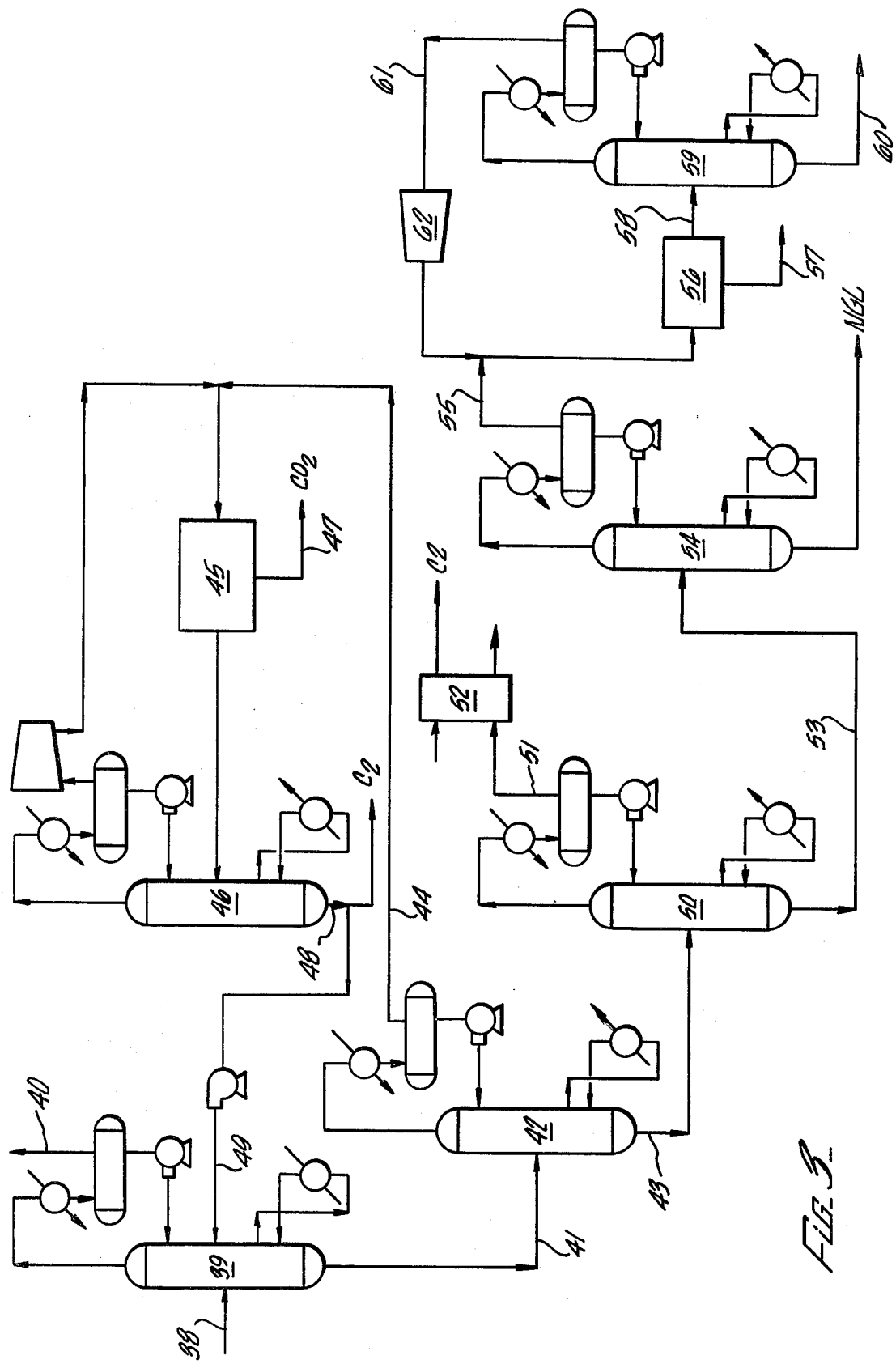

Referring to FIG. 3, a hydrocarbon stream of the following composition enters the process as stream 38 which is fed to distillation column 39 at a pressure of about 565 psia.

| $N_2$ | 0.5 Vol. % |
|---|---|
| $CH_4$ | 73.3 Vol. % |
| $CO_2$ | 12.6 Vol. % |
| $C_2$ | 6.4 Vol. % |
| $H_2S$ | 1.0 Vol. % |
| $C_3$ | 3.5 Vol. % |
| $C_4$ and higher | 2.7 Vol. % |

The coldest temperature within column 39 is approximately $-115°$ F. Methane is taken as the principal overhead product stream 40 and has the following approximate composition:

| 0.6 Vol. % | $N_2$ |
|---|---|
| 95.2 Vol. % | $CH_4$ |
| 1.8 Vol. % | $CO_2$ |
| 2.4 Vol. % | $C_2$ |
| TR | $H_2S$ |

The bottoms product 41 is fed to a second distillation column 42 at a pressure only slightly less than the first distillation column as a result of frictional losses, about 535 psia. The distillation column is operated in such a manner as to have all the $H_2S$ present in the bottoms product 43 and most, if not all, the $CO_2$ present in the overhad stream 44. In this example, the overhead product has the following composition:

| Ethane | 63 Vol. % |
|---|---|
| $CO_2$ | 37 Vol. % | and is fed to a membrane separation plant 45 and third distillation column 46 which produces the approximate $CO_2$-ethane azeotrope overhead for recycle in a manner analogous to Examples I and II. A 98% $CO_2$ stream 47, is produced from the membrane plant and the bottoms product 48 of the third distillation contains the ethane and propane, a portion of which 49 is returned to the first distillation column 39 to prevent $CO_2$ freezing.

The bottoms product 43 of distillation 42 is fed to a fourth distillation 50, and $CO_2$ and/or ethane with a small amount of $H_2S$ (the binary azeotrope of $H_2S$ and ethane at 515 psia is approximately 15% $H_2S$ 85% $C_2$ ethane) is produced as the overhead product 51. Because of the small volume of acid gas in this stream 51, it may be treated with caustic 52 to remove $H_2S$, and the ethane produced as a product or the entire stream 51 may be used for local fuel gas.

The bottoms product 53 of the fourth distillation step 50 contains all the remaining $H_2S$ and propane plus higher hydrocarbons. This stream is fed to a fifth distillation step 54. The overhead product 55 of the fifth distillation 54 contains all the $H_2S$ as the approximate azeotrope of $H_2S$ and propane;

| Propane | 20 Vol. % |
|---|---|
| $H_2S$ | 80 Vol. % |

The overhead product stream 55 is fed to a second membrane plant 56 at a pressure only slightly less than the fifth distillation column 54. The $H_2S$ passes through the membrane much more readily than propane. A stream 57 containing over 98% $H_2S$ is produced at a pressure of 5-10 psig required for further processing (e.g. in a Claus plant). The hydrocarbon gas passing over the membrane which does not permeate the membrane 58 is enriched in propane and exits the membrane system at a pressure only slightly less than the entrance pressure. The exit stream 58 has the following composition:

| $H_2S$ | 15 Vol. % |
|---|---|
| Propane | 85 Vol. % |

This stream 58 may be compressed to overcome frictional losses and returned to distillation column 54. If a separate propane product is desired, the stream is fed to a sixth distillation column 59 in which a bottoms product 60 of propane is produced. The overhead product 61 is again the approximate azeotrope of $H_2S$ and propane (80% $H_2S$ 20% propane) which is compressed 62 to overcome the small frictional losses and returned to the entrance of the second membrane system 56.

EXAMPLE IV

Figure 4:
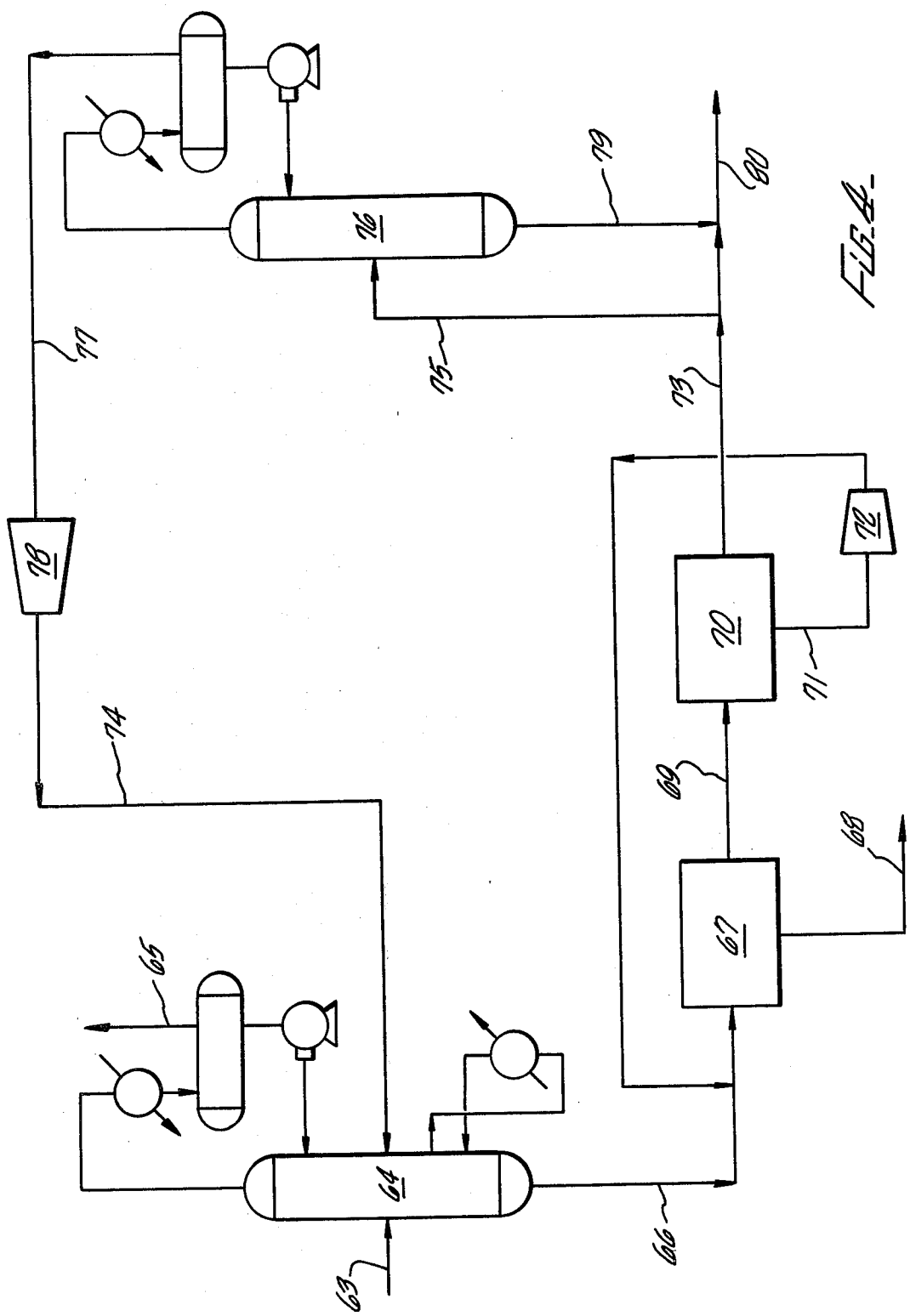

The first three examples show a variety of process schemes whereby the methane is first removed by distillation and membranes are used to significant economic advantage to remove acid gas components from resulting hydrocarbon streams. In Example IV, a plurality of membrane steps is used, and with less alternate processing, i.e., distillation, as shown in FIG. 4.

A hydrocarbon stream of the following composition enters the process as stream 63 which is fed to distillation volumn 64 at a pressure of about 565 psia.

| | |
|---|---|
| $N_2$ | .6 Vol. % |
| $CH_4$ | 95.2 Vol. % |
| $CO_2$ | 1.8 Vol. % |
| $C_2$ | 2.4 Vol. % |

The coldest temperature within column 64 is approximately $-115°$ F. Methane is taken as the principal overhead product stream 65 and has the following composition:

| | |
|---|---|
| $N_2$ | .5 Vol. % |
| $CH_4$ | 74.0 Vol. % |
| $CO_2$ | 12.7 Vol. % |
| $C_2$ | 6.5 Vol. % |
| $C_3$ | 3.5 Vol. % |
| $C_4$ and higher | 2.8 Vol. % |

The bottoms product 66 is fed to a membrane plant 67 at a pressure only slightly less than distillation column 64. Acid gas (in this Example $CO_2$ only) permeates the membrane more readily than the hydrocarbons. The acid gas is allowed to pass through the membrane until an acid gas stream is produced 68 with the maximum allowable hydrocarbon concentration. In this Example, the acid gas stream 68 has the following composition and is produced at a pressure of 5–10 psig required for venting or downstream processing:

| | |
|---|---|
| Ethane | 1.4 Vol. % |
| $CO_2$ | 98.0 Vol. % |
| Propane and heavier | .6 Vol. % |

The gas 69 rich in hydrocarbons but still containing considerable acid gas is at a pressure only slightly less than the feed stream 66, and is fed to a second membrane plant 70. The surface area and residence time are controlled so that a stream 73 containing 98% hydrocarbons is produced at a pressure only slightly less than the entrance to the second membrane plant 70.

The gases 71 which have passed through the membrane 70 are enriched in acid gas and at a lower pressure which may be varied to the desired process economics (i.e., higher pressure [lower pressure drop] will require greater membrane surface but save recompresion costs). This stream 71 has the following composition when cellulose acetate membranes are used and is compressed 72 to a pressure slightly greater than the entrance to the first membrane plant 67 and recycled to the entrance of the first membrane plant 67:

| | |
|---|---|
| $C_2$ | 20.9 Vol. % |
| $CO_2$ | 70.5 Vol. % |
| $C_3$ Plus | 8.6 Vol. % |

If the hydrocarbon stream 73 is processed further to separate components, the necessary recycle 74 to the distillation column 64 to prevent $CO_2$ freezing may come from one of these component streams. However, a portion 75 of the hydrocarbon stream 68 may be fed to a distillation column 76 to provide the $CO_2$ freezing prevention stream. The overhead product 77 of this distillation is mostly ethane with the following composition:

| | |
|---|---|
| Ethane | 90 Vol. % |
| Propane | 10 Vol. % | which is compressed 78 to overcome frictional losses and recycled to distillation column 64 as the $CO_2$ freeze preventor stream 74. The bottoms product 79 of distillation 76 is a liquid stream containing propane and heavier component plus some ethane is returned to the hydrocarbon liquid product stream 80.

What is claimed is:

1. A process of separating acid gases from hydrocarbons comprising separating methane from a hydrocarbon stream containing acid gases to produce a hydrocarbon stream substantially free from methane, and subsequently passing said substantially methane free hydrocarbon stream through a semipermeable membrane system to separate said acid gases from said hydrocarbon components, said acid gases passing through said membrane system at a substantially greater permeation rate than said hydrocarbon components.

2. The process of claim 1 in which methane is separated from said hydrocarbon stream by distillation and a portion of said substantially methane free hydrocarbon stream, after passing through said membrane system, is recycled to said distillation to prevent carbon dioxide from freezing therein.

3. The process of claim 2 in which said substantially methane free hydrocarbon stream is subjected to a distillation procedure from which the overhead product is an approximately binary azeotrope of carbon dioxide and ethane which is passed through said semipermeable membrane system to separate carbon dioxide therefrom and to produce an ethane rich stream.

4. The process of claim 3 in which said ethane rich stream is subjected to a further distillation and the ethane is recovered therefrom and recycled to said first distillation to prevent carbon dioxide from freezing therein.

5. The process of claim 2 in which said acid gases consist essentially of carbon dioxide and hydrogen sulfide.

6. The process of claim 5 in which said substantially methane free hydrocarbon stream is subjected to a distillation procedure and the overhead product thereof contains said acid gases, ethane and a portion of the heavier hydrocarbon content of said hydrocarbon stream, which is passed through said semipermeable membrane system to separate said acid gases and to yield a hydrocarbon rich stream.

7. The process of claim 6 in which said hydrocarbon rich stream is subjected to a further distillation from which a product stream containing ethane and said heavier hydrocarbon components is recovered and recycled to said first distillation to prevent carbon dioxide from freezing therein.

8. The process of claim 6 in which the hydrogen sulfide content of said hydrocarbon stream is removed from said first distillation as the bottom product and subjected to a further distillation procedure from which it is separated as the bottoms product which also contains propane and heavier hydrocarbons.

9. The process of claim 8 in which said bottoms product containing hydrogen sulfide, propane and heavier hydrocarbons, is subjected to an additional distillation from which hydrogen sulfide is removed as an overhead product of an approximate azeotrope of hydrogen sulfide and propane and fed through a semipermeable membrane system whereby the hydrogen sulfide is separated and recovered therefrom and a propane rich stream is produced.

10. The process of claim 9 in which said propane rich hydrocarbon stream is removed from said semipermeable membrane step and subjected to further distallation from which propane is recovered.

11. The process of claim 2 in which said substantially methane free hydrocarbon stream is passed through a first semipermeable membrane whereby acid gases are separated therefrom and the hydrocarbon rich stream remaining is thereafter passed through a second semipermeable membrane system to remove remaining acid gases.

12. The process of claim 11 in which said hydrocarbon rich stream is subsequently subjected to a distillation step from which the ethane component is separated as the overhead product and recycled to said first distillation to prevent carbon dioxide from freezing therein.

13. The process of claim 12 in which propane and heavier hydrocarbon components are removed and recovered as the bottoms product from said second distillation.

14. The process of claim 2 in which said acid gases consist essentially of carbon dioxide, said substantially methane free hydrocarbon stream is subjected to a distillation procedure and the overhead product thereof contains carbon dioxide, ethane and a portion of the heavier hydrocarbon content of said hydrocarbon stream, which is passed through said semipermeable membrane system to separate said carbon dioxide and to yield a hydrocarbon rich stream.

15. A process of separating acid gases from hydrocarbons comprising subjecting a hydrocarbon stream containing carbon dioxide and/or hydrogen sulfide to low temperature distillation to produce a hydrocarbon stream substantially free from methane, and subsequently passing said substantially methane-free stream through a semi-permeable membrane system to separate said acid gases from said hydrocarbon components and to produce a hydrocarbon rich stream, said acid gases passing through said membrane system at a substantially greater permeation rate than said hydrocarbon components.

16. The process of claim 15 in which at least a portion of said hydrocarbon rich stream is recycled to said low temperature distillation to prevent carbon dioxide from freezing therein.

* * * * *